(12) United States Patent
Bonnefin et al.

(10) Patent No.: US 7,741,966 B2
(45) Date of Patent: Jun. 22, 2010

(54) PROXIMITY DETECTION APPARATUS

(75) Inventors: Wayne Lee Bonnefin, Neston (GB); Henrik Landahl, Lund (SE); Roland Larsson, Staffanstorp (SE)

(73) Assignee: ConvaTec Technologies Inc., Skillman, NJ (US)

( * ) Notice: Subject to any disclaimer, the term of this patent is extended or adjusted under 35 U.S.C. 154(b) by 467 days.

(21) Appl. No.: 11/626,079

(22) Filed: Jan. 23, 2007

(65) Prior Publication Data

US 2007/0247304 A1 Oct. 25, 2007

(30) Foreign Application Priority Data

Jan. 24, 2006 (GB) ................. 0601454.2

(51) Int. Cl.
*G08B 1/00* (2006.01)
(52) U.S. Cl. ................. 340/531; 340/686.6; 340/573.1; 606/202
(58) Field of Classification Search ................. 340/531, 340/686.6, 10.1, 10.2, 10.3, 573.1, 573.7; 606/202; 2/455, 465, 468
See application file for complete search history.

(56) References Cited

U.S. PATENT DOCUMENTS

| | | | |
|---|---|---|---|
| 4,638,307 A * | 1/1987 | Swartout ................. 340/666 |
| 5,443,440 A | 8/1995 | Tumey | |
| 5,626,129 A | 5/1997 | Klimm | |
| 6,296,617 B1 | 10/2001 | Peeler | |
| 6,447,538 B1 | 9/2002 | Van Duren | |
| 6,494,852 B1 * | 12/2002 | Barak et al. ................. 601/151 |
| 6,884,255 B1 * | 4/2005 | Newton ................. 606/202 |
| 7,017,195 B2 * | 3/2006 | Buckman et al. ................. 2/455 |
| 7,138,914 B2 * | 11/2006 | Culpepper et al. ..... 340/539.13 |
| 2005/0159690 A1 | 7/2005 | Barak | |

FOREIGN PATENT DOCUMENTS

| | | |
|---|---|---|
| EP | 0314306 | 5/1989 |
| EP | 1139827 | 3/2002 |
| EP | 1473013 | 11/2004 |
| GB | 2339927 | 2/2000 |
| WO | WO 2004/069060 | 8/2004 |
| WO | WO2004/091463 | 10/2004 |

* cited by examiner

*Primary Examiner*—Anh V La
(74) *Attorney, Agent, or Firm*—John M. Kilcoyne

(57) ABSTRACT

A proximity detection apparatus for a control unit for use in controlling a medical device, the proximity detection apparatus comprising: a detecting part and an emitting part; one part being located in the medical device and the other part in the control unit, so that when the control unit is attached to the medical device the detecting part detects the emitting part and instructs the control unit to select a first mode of operation and when the control unit is detached from the medical device, the detecting part does not detect the emitting part and instructs the control unit to select a second mode of operation.

16 Claims, 2 Drawing Sheets

PROXIMITY DETECTION APPARATUS

BACKGROUND OF THE INVENTION

This invention relates generally to a proximity detection apparatus. In particular, the invention relates to a proximity detection means for a detachable control unit for use with a medical device. Such medical devices include pressure offloading devices such as inflatable bed mattresses and inflatable cushions, and pressure application devices such as mobile compression devices.

Various compression devices are known for applying compressive pressure to a patient's limb. These types of devices are used to assist in the prevention of deep vein thrombosis (DVT), vascular disorders and the reduction of oedema. The majority of known devices are adapted for use in a hospital setting in which they are used predominantly for the prevention of DVT in patients with a high risk for developing this condition.

Compression therapy may be used in the treatment of patients with venous leg ulcers and compression of the limb achieved by a pneumatic or hydraulic compression device strapped to the patient. Known in the art are mobile compression devices comprising one or more air- or fluid-inflatable cuffs containing one or more cells arranged in an inflatable sleeve for fitting on to a foot, leg or an arm. By means of pressure sensors located in the cells, the device allows for the adjustment of the pressure in the cells of the cuffs dependent on whereabouts on the limb the application of more or less pressure is required during the course of a patient's therapy.

The application of pressure in the cells of the inflatable sleeve can be maintained by an air or fluid pump which is generally located in and operated by an automatic control unit. Accordingly, the pump will typically be associated with an air or fluid conduit system, valves and air or fluid inlet ports. The automatic control unit will typically be a separate component to the sleeve and be electrically powered. Where excessive or deficient pressure is detected by a pressure sensor located in a particular cell, the control unit can activate the pump to restore the intended localized pressure. The control unit will also typically contain the electronic circuitry, air conduits and valves to assist in performing the function of modulating the air or fluid pressure in the cells of the compression device.

In addition to the above-mentioned features, the control unit will generally contain a display (such as a liquid crystal display (LCD)) which provides information to the user or healthcare professional concerning the device.

The control unit may also contain computer hardware containing programmable software for inputting a patient's precise compression therapy requirements. That is, prescribed air or fluid pressure levels throughout the compression device at designated times and for designated periods. Accordingly, a specific therapy for a particular patient can be programmed into the control unit to avoid the need for the patient to manually operate the unit.

The software may also be adapted to keep a record of the pressure in the device over time, thus giving the healthcare professional access to a compliance record of the patient's course of therapy.

A disadvantage of having different modes of use available from a single unit is that it is necessary to switch between the modes in order to obtain the desired function. For instance, for the patient to have a functioning device it is necessary for the control unit to operate the device to provide the selected pressure profile to the limb. For the healthcare professional to obtain compliance data from the device it is necessary for the control unit to display compliance data and not operate the device.

We have now found that it is convenient for the control unit to select between these modes dependent on whether it is present on the device it is operating. In this way, the device can operate in a patient mode to operate the device when present on the device, and in a healthcare professional mode to display compliance data when it is detached from the device.

SUMMARY OF THE INVENTION

According to the invention there is provided a proximity detection apparatus for a control unit for use in controlling a medical device, the proximity detection apparatus comprising:
(i) a detecting part, and
(ii) an emitting part one part being located in the medical device and the other part in the control unit, so that when the control unit is attached to the medical device the detecting part detects the emitting part and instructs the control unit to select a first mode of operation and when the control unit is detached from the medical device, the detecting part does not detect the emitting part and instructs the control unit to select a second mode of operation.

Further, according to the invention, there is provided a proximity detection apparatus for a detachable control unit for use in controlling a medical device, the proximity detection apparatus comprising:
(i) a detecting part, and
(ii) an emitting part, one part being located in the medical device and the other part in the control unit such that the detecting part is adapted for detecting the emitting part, wherein when the control unit is detached from the medical device the detecting part does not detect the emitting part and instructs the control unit to select a mode of operation comprising means for displaying data relating to medical device usage.

The apparatus of the invention allows for a control unit to be specifically adapted for use with a particular type of medical device. This may be achieved by having a detecting part which is specific to the emitting part such that when the detecting part detects the emitting part, the control unit operates the medical device. When the detecting part no longer detects the emitting part (i.e., when they are detached) the control unit does not operate the medical device.

This has the advantage that in the second mode where the control unit is de-activated, certain functions of the control unit no longer operate (e.g., a pressure control system). Therefore, electrical power is preserved. Where a portable battery source is used to power the control unit and, consequently, operate the medical device, longer battery life results.

A further advantage is where the medical device comprises inflatable components driven by a pump in the control unit. The pump will typically draw air or liquid from an external source (e.g., atmospheric air or an hydraulic fluid reservoir) to inflate the inflatable components. By de-activating the control unit once it has been detached from the medical device, the pump may be de-activated. This reduces the risk of contamination of the control unit (and the medical device which it operates) from the external source as the pump is not pumping air or fluid.

By enabling selection between the first and second modes, the apparatus provides a means allowing for different modes of use of the control unit dependent on whether the control unit is attached or detached from the medical device. This provides a convenient and practical means for switching between patient and healthcare professional modes in a control unit for a medical device.

Further, according to the invention, there is provided a medical device comprising a proximity detection apparatus according to the invention. Preferably, the device is an inflatable bed mattress, inflatable cushion or a mobile compression device.

Even further, according to the invention there is provided a mobile compression device for a limb comprising an inflatable sleeve for placing on a limb, a control unit for controlling the air or fluid pressure in the inflatable sleeve and a proximity detection apparatus according to the invention.

Preferably, when the control unit is attached to the device, the control unit operates the device in a "patient" mode. The "patient" mode is where the control unit is operating the medical device, for instance to conform with a patient's therapy.

Preferably, when the control unit is detached from the device the control unit operates the device in a "healthcare professional" mode. The "healthcare professional" mode is where the control unit no longer acts to operate the medical device, but rather has reverted to a mode where data relating to use of the medical device (compliance) can be displayed for the healthcare professional to review. In the second mode, the control unit is detached from the medical device providing a convenient means for the healthcare professional to remotely analyze data relating to device usage and, hence, patient compliance.

Data which can be displayed may relate to any one or more of the duration of use of the device, the mode of operation of the device, and where the device is a mobile compression device, the pressure exerted by a sleeve on a limb. Further details regarding data and data collection relevant to the present invention are described in GB Patent Application No. 0515040.4.

As the apparatus of the invention provides a convenient means for switching between the patient and healthcare professional modes, the healthcare professional does not have to manually switch the control unit from the patient mode in order to retrieve usage data during a patient consultation. Rather, the healthcare professional simply detaches the control unit from the medical device, thereby switching to the healthcare professional mode. This is particularly advantageous where the control unit is attached to the device and worn by the patient. If not detachable, the whole device would have to be removed from the patient in order for the professional to interrogate the control unit and obtain the compliance data. To revert to the patient mode, the healthcare professional re-attaches the control unit on the medical device to switch back to the original mode.

Preferably, the emitting part is a magnet located in or on the medical device. Even more preferably, the magnet is mountable within or on an outer surface of the medical device. By mounting the magnet within or on the outer surface of the medical device, such as the inflatable sleeve of a mobile compression device, the electronic components of the apparatus may be housed along with the control unit, while non-electronic components such as a magnet and an inflatable sleeve can be separately integrated.

More preferably, the magnet is a permanent magnet. The positioning of a permanent magnet underneath the outer surface of the medical device, such as the inflatable sleeve of a compression device, has the advantage that the magnet can be readily integrated as part of the device during its manufacture. Consequently, the magnet can be fixed in a desired position in the device and cannot be easily shifted within or removed from the device.

Fixed positioning of the emitting part (e.g., a magnet) on the device has the advantage that with fixed positioning of the detecting part (e.g., magnetic sensor) on the control unit, the emitting and detecting parts can be suitably aligned with one another when the control unit is positioned in a fixed predetermined manner on a medical device during normal operation.

This has the added advantage that control unit/medical device arrangements can be assembled where a control unit is specific to a particular medical device. That is, the respective positioning of the emitting and/or detecting part can be arranged so that a control unit specific to operate one device will not operate another device because the emitting and detecting parts do not align. Hence, the operating mode is not activated and the patient mode operating the medical device is prevented. This has particular benefit where a standard control unit type is employed to operate different types of medical devices or even the same medical device configured to suit a particular patient's needs. Detection being achieved solely by modifying the relative physical positioning of the emitting and detecting parts.

Preferably, a magnetic sensor is used as the detecting part in combination with a magnet as the emitting part. A magnetic sensor is able to facilitate switching between modes by the presence or absence of a magnetic field. Preferably, the magnetic sensor will be a Hall sensor SNS2. This is an omnipolar sensor, hence, the polarity of the magnetic field does not matter. The sensing distance of the Hall sensor SNS2 is approximately 20 mm and the output is open drain. The sensor is connected directly to the control unit and utilizes a pull up resistor present at the control unit input.

In other embodiments, the magnet and magnetic sensor are unique to one another, i.e., a specific magnet will only be recognized by a sensor of a complementary or compatible type. This means that there is a significant reduction in the likelihood of the wrong control unit being applied to a medical device. This is because if a user brings together a non-compatible magnet and magnetic sensor, the control unit will not activate and operate the device. This avoids the risk of a control unit programmed with particular settings being erroneously applied to the device for a particular patient.

While the use of a magnet and magnetic sensor is preferred as emitting and detecting parts, other sensing means may be effectively applied to the invention. These include inductive sensors, optical sensors, radio-frequency ID tagging sensors, mechanical sensors and bar code sensing arrangements.

Preferably, the detecting part of the proximity detection apparatus comprises a reed switch. A reed switch is an electric switch comprising a pair of ferrous metal contacts in a hermetically sealed glass envelope. A magnetic field emitted from a permanent magnet or electromagnet in close proximity to the reed switch causes the metal contacts to pull together, thus completing an electrical circuit. The completion of the electrical circuit operates to switch the apparatus to the first position where the control unit is activated to operate the medical device. By withdrawing the magnet from the reed switch the metal contacts separate which disrupts the electrical circuit. This switches the apparatus to the second mode where the control unit no longer operates the medical device but activates the "healthcare professional" mode.

Preferably, the apparatus comprises a control unit which in the healthcare professional mode comprises a means for displaying patient usage data. Even more preferably, in the patient mode, the control unit comprises a means for displaying in situ functional data relating to the operation of a medical device being worn by a patient. By way of example, this may be data relating to temperature, pressure, etc., in a mobile compression device with an inflatable sleeve.

Preferably, the medical device associated with the apparatus of the invention is a single medical device.

The inflatable sleeve of the compression device, preferably, comprises more than one individually inflatable cell. More preferably, a sensor is associated with each cell in the sleeve to monitor the pressure experienced by the limb due to pressure from that cell. This allows the device to precisely control the pressure in each cell and thus comply with a predetermined compression therapy profile designated by a healthcare professional. This arrangement allows the device to operate a peristaltic or static compression routine which can be a preferred means of compression therapy.

The provision of individual cells in the sleeve and sensors constantly monitoring pressure exerted by the sleeve allows the device to be dynamic. An advantage of this dynamic feature of the device is that the effectiveness of venous return is maintained whatever the patient does.

Preferably, the medical device comprises a pouch located on its outer surface for tightly holding the control unit in place when the device is being operated. This has the benefit of providing a low profile and secure means of connecting the control unit to the medical device. It also allows the control unit to be easily attached and detached from the device.

More preferably, the control unit is adaptable for connection to a backing plate attached to the medical device, preferably on an inner surface of the pouch. In this embodiment, the backing plate contains either the emitting or detecting parts of the apparatus of the invention.

Most preferably, the medical device contains a backing plate wherein the emitting part is located on the surface of the backing plate. The backing plate is attached to the sleeve and the control unit is a separate item which can be positioned on the backing plate by a sliding mechanism. The backing plate may include a sliding mechanism which can be adapted so that when the control unit is attached to the backing plate, the emitting part on the backing plate becomes positioned adjacent to a detecting part in the control unit, thereby enabling the mode switch.

In other embodiments, the control unit can be positioned separately from the medical device, such as in a docking station with umbilical connections carrying air or fluid to the medical device.

Preferably, the control unit comprises a programmable microprocessor control system. More preferably, the control unit comprise a display device, such as an LCD, arranged to provide a display of data gathered from sensors in the sleeve both current and over a period of time. The data gathered can also include the number of hours of use in normal mode and intermittent pneumatic compression (IPC) mode. Such information can be hidden from display in the patient mode. Alternatively, the sleeve can have a clear window aligned with the display device so that the patient and healthcare professional can observe displayed data while the device is in situ and without having to detach the control unit from the device.

Preferably, the display device shows the current pressure (or other relevant data) in the cells of the sleeve when the control unit is in the operating mode. More preferably, the display device shows the pressure history of the compression device over the course of the compression therapy. Most preferably, the control unit in the disabled mode has the facility whereby it may be connected to a computer to permit a print out (e.g., paper) of the pressure history of the compression device to be made.

Preferably, the control unit is light-weight, portable and wearable so that it is comfortable and not cumbersome for the patient. More preferably, the control unit is worn attached to the inflatable sleeve. The control unit may also contain a power source, such as a re-chargeable battery, a series of conduits leading to outlets connectable to a further set of conduits in the sleeve, each relating to a cell in the sleeve. The conduits are for air or fluid transfer from an air or fluid inlet port in the control unit to the cells in the sleeve.

Preferably, when the second mode of the control unit is implemented by detaching the control unit from the inflatable sleeve of the compression device, the control unit automatically provides a means for displaying pressure modifications in the inflatable sleeve over the period of the compression therapy. This allows the healthcare professional in the clinical environment to quickly and easily obtain a data readout of the pressure levels throughout the cells of the sleeve over a designated period of therapy. Using a series of input buttons on the control unit, the user can request details of the various aspects of the recent use of the compression device. To avoid tampering with the control unit, access to the data may be obtainable only by the input of a unique personal identification number (PIN).

This direct monitoring of the use of a compression device allows the healthcare professional to gain a rapid indication of the patient's compliance with the prescribed therapy. This is particularly useful where a patient has been treated at home or not in a hospital setting.

Preferably, the control unit is received on an outer surface of the inflatable sleeve. The provision of a pouch allows the control unit to be easily attached and detached from the inflatable sleeve. Consequently, this allows for the alignment and magnetic connection of the magnet and the magnetic sensor and thus easy switching of the control unit between modes by withdrawing the control unit from the pouch.

Preferably, the device comprises an inflatable sleeve comprising more than one inflatable cell. More preferably, it comprises four cells. The number and shape of the cells in the inflatable sleeve is dependent on the requirements of the patient and the limb to which the sleeve is to be applied. Preferably, the inflatable sleeve of the device of the invention is adapted for use on a leg, foot or an arm.

Further, according to the invention, a method of detecting the proximity of a control unit of a medical device is provided, comprising the steps of:
 (i) attaching the control unit to the medical device;
 (ii) providing a signal from an emitting part;
 (iii) sensing the signal from the emitting part;
 (iv) providing the sensed signal to a control unit; and
 (v) configuring the control unit to operate the device.

Even further, according to the invention, a method of detecting the proximity of a control unit of a medical device is provided, comprising the steps of:
 (i) attaching the control unit to the medical device so that the control unit operates the device;
 (ii) detaching the control unit from the medical device, thereby sensing the absence of the control unit from the medical device;
 (iii) providing a signal that the medical device is absent; and
 (iv) configuring the control unit to cease operation of the device and display data relating to the use of the device.

DETAILED DESCRIPTION OF THE INVENTION

Figure 1:
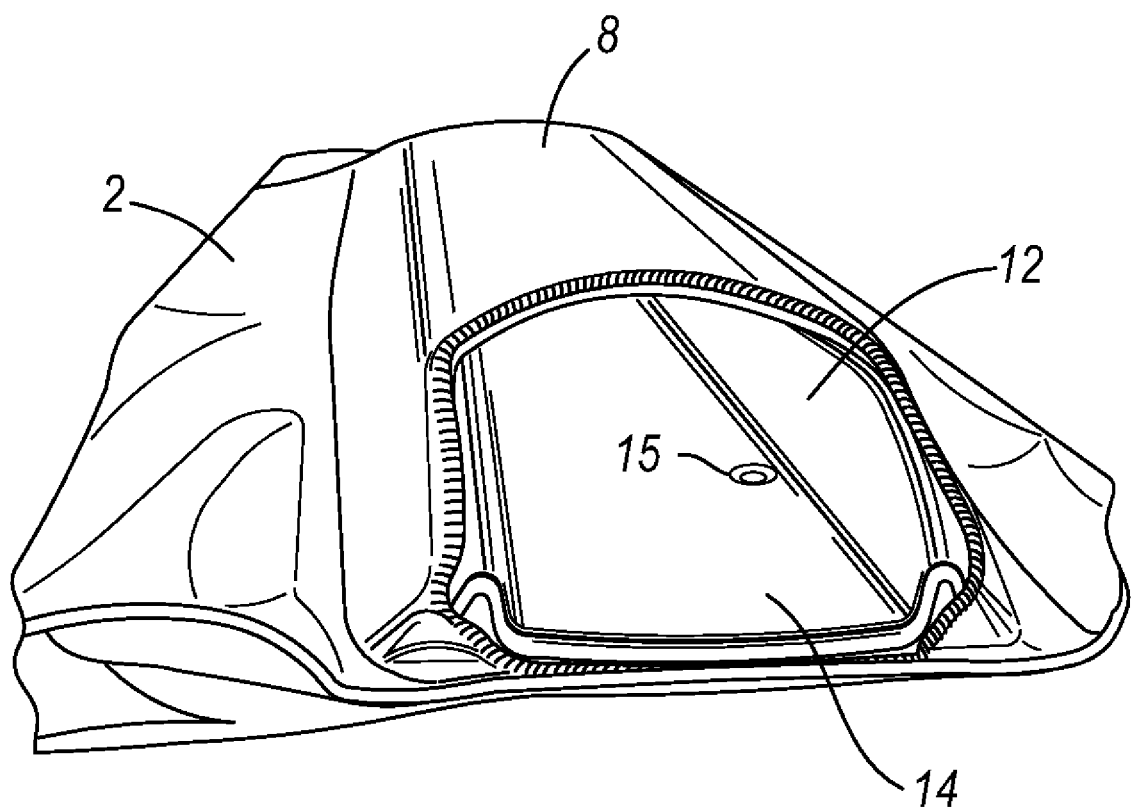
FIG. 1 is a perspective view of a pouch for receiving a control unit, the pouch being integrated in a mobile compression device to be worn on the limb of a patient and comprising the emitting part of a proximity detection apparatus of the invention.

In FIG. 1, an inflatable mobile compression device 2 comprises a pouch with an outer surface 8 and an inner surface 12. Situated on inner surface 12 is a rigid backing plate 14. Backing plate 14 possesses a series of rigid connectors 16 (see FIG. 3) for connecting a control unit 10 (see FIG. 2) to compression device 2. The control unit 10 typically comprises a power source and an air or fluid pumping means for inflating compression device 2 when being worn by a patient. Situated on backing plate 14 is magnet 15, which acts as the emitting part of the proximity detection apparatus of this embodiment of the invention.

Figure 2:
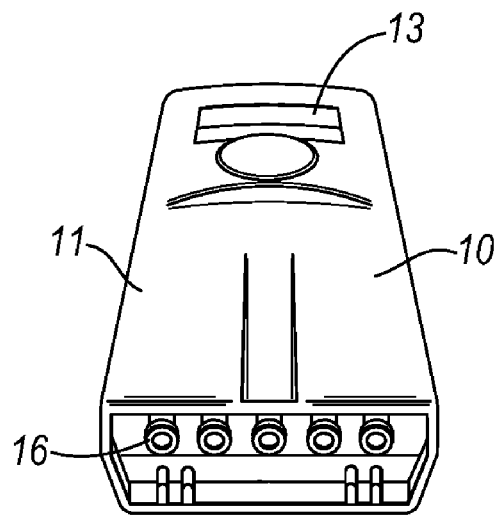
FIG. 2 is a perspective view of a control unit for a mobile compression device which is suitable for use according to the invention.

In FIG. 2, control unit 10 comprises front face 11 which comprises display 13. Display 13 is adapted for displaying data concerning the functioning of the combination of control unit 10 with mobile compression device 2. Control unit 10 also comprises rigid connectors 16 for connection with complementary rigid connectors of backing plate 14 (see FIGS. 1 and 3).

Figure 3:
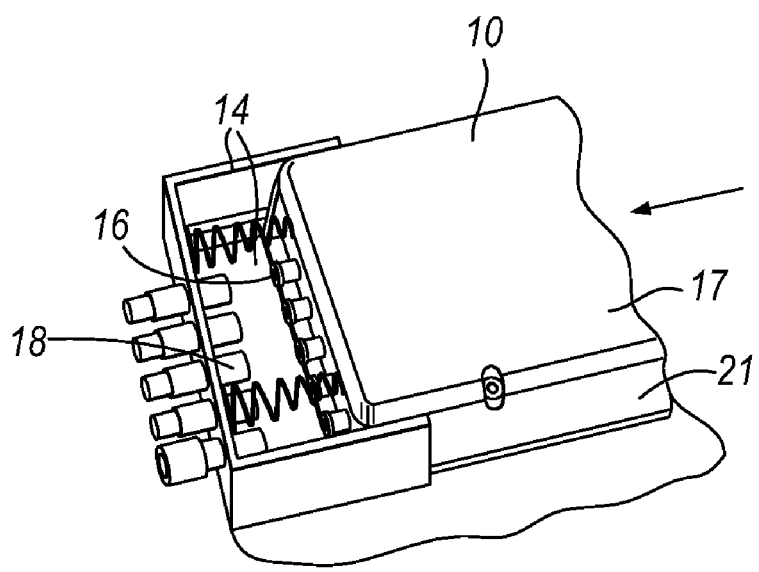
FIG. 3 is a perspective partial view of a backing plate present in the pouch of FIG. 1, here removed from the pouch for illustration and the control unit of FIG. 2, wherein the control unit comprises the detecting part of a proximity detection apparatus of the invention.

FIG. 3 shows the connectivity of control unit 10 (partial view) and backing plate 14 (partial view) of compression device 2. Control unit 10 comprises back face 17 and side face 21 (both obscured in FIG. 2). To connect control unit 10 to backing plate 14 and, hence, mobile compression device 2, control unit 10 is inserted in the pouch defined by outer surface 8 and inner surface 12 by sliding control unit 10 along backing plate 14 (along the direction of the arrow) until rigid connectors 16 slot into rigid connectors 18. Once the control unit 10 is in place, a magnetic sensor (not shown—concealed beneath back face 17) as the detecting part is in alignment with magnet 15 located on backing plate 14. This results in a magnetic switch being activated by the alignment of magnet 15 and the magnetic sensor (not shown), thereby activating the control unit 10 to adopt a patient mode and operate mobile compression device 2. By manually withdrawing the control unit 10 from the pouch (reverse direction of the arrow), the alignment of magnet 15 and the magnetic sensor (not shown) is disrupted and control unit 10 adopts the healthcare professional mode which results in the mobile compression device 2 no longer operating. Data on patient usage can then be recorded by the healthcare professional from display 13 of control unit 10.

We claim:

1. A proximity detection apparatus for a control unit for use in controlling a medical device, the proximity detection apparatus comprising:
    (i) a detecting part, and
    (ii) an emitting part,
one part being located in the medical device and the other part in the control unit, so that when the control unit is attached to the medical device the detecting part detects the emitting part and instructs the control unit to select a first mode of operation wherein the control unit operates the medical device in a patient mode to conform with the patient's therapy and when the control unit is detached from the medical device, the detecting part does not detect the emitting part and instructs the control unit to select a second mode of operation wherein data relating to use of the medical device and patient compliance is displayed.

2. The proximity detection apparatus of claim 1, wherein the emitting part is a magnet mountable within or on an outer surface of the medical device.

3. The proximity detection apparatus of claim 2, wherein the magnet is a permanent magnet.

4. The proximity detection apparatus of claim 1, wherein the medical device is a single medical device.

5. A medical device comprising the proximity detection apparatus of claim 1.

6. The medical device of claim 5, wherein the medical device is an inflatable bed mattress, inflatable cushion or a mobile compression device.

7. A mobile compression device for a limb comprising an inflatable sleeve for placing on a limb, a control unit for controlling the air or fluid pressure in the inflatable sleeve and the proximity detection apparatus of claim 1.

8. The mobile compression device of claim 7, wherein the detecting part comprises a magnetic sensor.

9. The mobile compression device of claim 7, wherein the control unit comprises an air or fluid pump, a valve, an air or fluid conduit for supplying air or fluid to the inflatable sleeve, a microprocessor and a memory.

10. The mobile compression device of claim 7, wherein an outer surface of the inflatable sleeve comprises a pouch for receiving the control unit.

11. The mobile compression device of claim 7, wherein the inflatable sleeve comprises more than one inflatable cell.

12. The mobile compression device of claim 7, wherein the limb is a leg, foot or an arm.

13. A proximity detection apparatus for a detachable control unit for use in controlling a medical device, the proximity detection apparatus comprising:
    (i) a detecting part; and
    (ii) an emitting part,
one part being located in the medical device and the other part in the control unit such that the detecting part is adapted for detecting the emitting part, wherein when the control unit is detached from the medical device the detecting part does not detect the emitting part and instructs the control unit to select a mode of operation wherein data relating to medical device usage and patient compliance is displayed.

14. The proximity detection apparatus of claim 13, wherein the emitting part is a magnet mountable within or on an outer surface of the medical device.

15. A medical device comprising the proximity detection apparatus of claim 13.

16. A method of detecting the proximity of a control unit of a medical device, comprising the steps of:
    (i) attaching the control unit to the medical device so that the control unit operates the device;
    (ii) detaching the control unit from the medical device, thereby sensing the absence of the control unit from the medical device;
    (iii) providing a signal that the medical device is absent; and
    (iv) configuring the control unit to cease operation of the device and display data relating to the use of the device.

* * * * *